United States Patent [19]

Morel

[11] 4,424,399
[45] Jan. 3, 1984

[54] UNSATURATED FATTY ALCOHOLS AND METHOD OF PREPARING THEM

[75] Inventor: Didier Morel, Lyons, France

[73] Assignee: Rhone-Poulenc Industries, Paris, France

[21] Appl. No.: 185,593

[22] Filed: Sep. 9, 1980

[30] Foreign Application Priority Data

Sep. 14, 1979 [FR] France .................................. 79 22976

[51] Int. Cl.$^3$ .............................................. C07C 33/02
[52] U.S. Cl. ................................ 568/840; 260/459 R;
568/384; 568/408; 568/618; 568/881; 568/903
[58] Field of Search .......................................... 568/840

[56] References Cited

U.S. PATENT DOCUMENTS 3,887,627 6/1975 Romanelli .
3,925,485 12/1975 Chabardes et al. .................. 568/840
4,006,193 2/1977 Ninagawa et al. .................. 568/840

FOREIGN PATENT DOCUMENTS 1139488 11/1962 Fed. Rep. of Germany .
2148156 3/1972 Fed. Rep. of Germany .
2039652 1/1971 France .
2045369 2/1971 France .
2266682 10/1975 France .

Primary Examiner—J. E. Evans

[57] ABSTRACT

New unsaturated fatty alcohols of the formula:

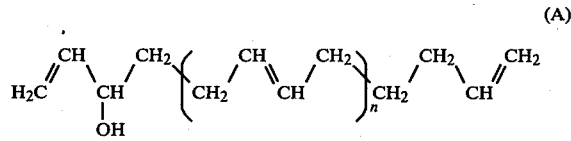

(A)

in which n=2 or 4 are provided and are prepared by the novel process of reacting butadiene with water in the presence of a palladium salt and orthoboric acid, $B(OH)_3$, in a polar aprotic solvent.

3 Claims, No Drawings

UNSATURATED FATTY ALCOHOLS AND METHOD OF PREPARING THEM

The present invention relates to new unsaturated fatty alcohols and to a novel process for preparing them.

It is an object of the present invention to provide novel unsaturated fatty alcohols.

It is a further object to provide a novel process of preparing the novel unsaturated fatty alcohols of the invention.

Further objects will be apparent to those skilled in the art from the present description.

GENERAL DESCRIPTION OF THE INVENTION

The compounds of the invention have the general formula ("A") shown below:

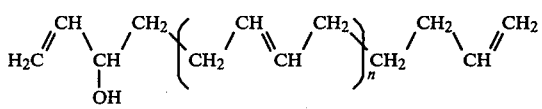
(A)

in which n is equal to 2 or 4.

The invention therefore concerns more particularly the novel compounds: hexadeca-1,6,10,15-tetraen-3-ol (n=2) and tetracosa-1,6,10,14,18,23-hexaen-3-ol (n=4).

The invention also has as its object a process of preparing compounds of formula "A" comprising reacting butadiene with water in the presence of a palladium salt and orthoboric acid, $B(OH)_3$, in a polar aprotic solvent.

In accordance with one particular embodiment of the process of the invention, a carboxylic acid is present in the polar aprotic solvent simultaneously with the palladium salt and the orthoboric acid.

It should be emphasized that, within the present invention, the addition of and presence of carboxylic acid is not necessary. However, it makes it possible to increase the stability of the catalytic system formed from the palladium salt. It also makes it possible to increase the selectivity for the alcohol of the formula (A) in which n=2.

The palladium salt is selected preferably from the group comprising palladium carboxylates of the formula ("B"): $(R_1COO)_2Pd$, the allyl complexes of palladium having a carboxylate radical of the formula ("C"): $(R_2PdR_1COO)_2$, and the allyl complexes of palladium having the formula ("D"); $R_2PdOR_1$ in which:

$R_1$ represents a radical selected from the group comprising alkyl radicals having from about 1 to 6 carbon atoms, such as the methyl, ethyl, isopropyl, and n-butyl radicals and aryl radicals, such as the phenyl, tolyl, benzyl and naphthyl radicals, these radicals being optionally substituted.

$R_2$ represents a radical of the formula:

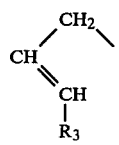

in which $R_3$ represents a hydrogen atom or the radical $R_1$.

As examples of palladium carboxylates of formula ("B") which can be used in the process of the invention, mention may be made of palladium acetate and palladium benzoate.

As examples of allyl complexes of palladium of formula ("C") which can be used in the process of the invention, mention may be made of the compounds of the following structures:

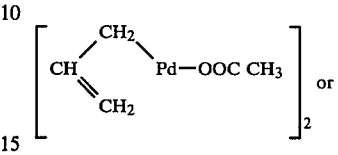

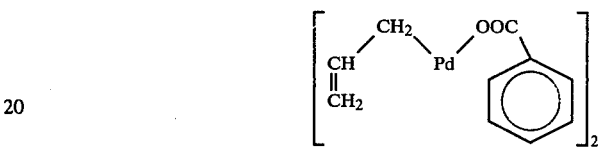

As example of complex of formula ("D") one may mention the compound of the formula:

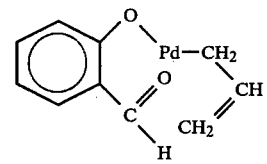

The solvent is selected preferably from the group of aprotic solvents comprising dimethylformamide, hexamethylphosforus triamide, dimethylacetamide and N-methylpyrrolidone.

The carboxylic acid optionally used in the process of the present invention has the general formula $R_4COOH$, in which $R_4$ represents a radical selected from among the group comprising the alkyl and aryl radicals, optionally substituted.

In accordance with one particular embodiment of the process of the invention, there is employed a carboxylic acid of the formula $R_4COOH$, in which $R_4$ represents an acrylic or cyclic alkyl radical having from about 1 to 12 carbon atoms. Mention may be made in particular of the acids of the following formulae:

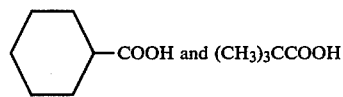

In accordance with another specific embodiment of the process there may be employed a carboxylic acid of the formula $R_4COOH$ in which $R_4$ represents a radical having a formula selected from the group comprising of:

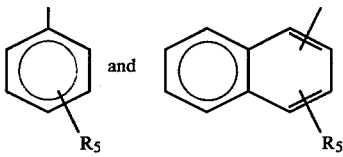

in which R₅ represents a radical selected from the group comprising hydrogen, OH, and the alkyl radicals having from about 1 to 12 carbon atoms.

Mention may be made in particular of the acids of the following structural formulae:

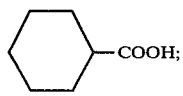

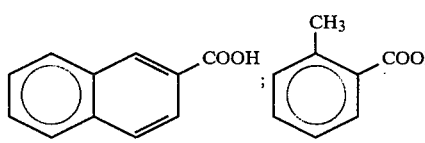

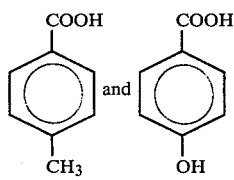

In the process of the invention a temperature between about −5° C. and about +150° C. is generally employed. The temperature is preferably selected from between about 10° C. and 35° C. when operating without the addition of a carboxylic acid. When operating in the presence of the latter, the temperature is preferably between about 50° C. and 100° C.

The use of a carboxylic acid, which increases the stability of the catalyst system, makes it possible to carry out the reaction at a higher temperature. This results in an increase in the reaction velocity and, therefore, an increase in the yield of the desired alcohol.

The molar ratio of butadiene to water employed in the process is preferably between about 0.1 and 10:1. More particularly, it is preferred to use the butadiene and the water in a molar ratio close to about 1:1. The ratio of the number of mols of butadiene to the number of gram-atoms of palladium is generally between about 100 and about 1000 to 1. A value of close to 300:1 is preferred. Values less than or greater than this range are not excluded since they do not affect the selectivity, but only the reaction velocity. In order to obtain the best selectivity, one preferably operates with a molar ratio of water to boric acid, B(OH)₃, of between about 0.1 and about 20:1. Even more preferably, there is used a molar ratio of H₂O to B(OH)₃ of between about 2 and about 10:1.

The ratio of the number of mols of carboxylic acid to the number of gram-atoms of palladium is preferably between about 0.5 and about 20:1. Even more preferably it is between about 2 and about 6:1.

It is preferred to carry out the process of the invention in a homogeneous medium. The boric acid will therefore be used in an amount which does not exceed the limit of solubility (250 g/l of solvent approximately at room temperature). The amounts of boric acid are therefore determined by the amounts of solvent. The latter must be sufficient for the butadiene to be soluble in the water-solvent mixture.

The process of the invention is desirably conducted at autogenous pressure, although pressures greater or less than autogenous pressure are not excluded from the invention.

The reaction time, when operating within the above-indicated preferred temperature ranges, is preferably between about 1 and 30 hours. Beyond 30 hours, the formation of heavy compounds increases.

In order to decrease the formation of heavy compounds (oligomers of butadiene, non-functional polymers and polymers having alcohol functions) one may add a phosphine, such as triphenylphosphine, P(φ)₃, to the reaction system. A phosphine is preferably used in an amount such that the atomic ratio: P3+/Pd—is between about 0.1 and about 0.5:1. This ratio is preferably close to about 0.25:1.

The process of the invention can be carried out continuously or batchwise. The products obtained having the formula ("A") can be hydrogenated to form saturated linear alcohols of the following formula:

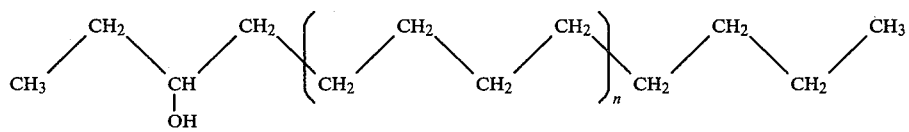

where n=2 or 4 as in formula ("A") above. This can be done by hydrogenation at a pressure of 50 bars of hydrogen employing pentane as the solvent at a temperature of about 20° C., employing a catalyst of palladium or platinum deposited on carbon black support in the amount of 10% of palladium or platinum. Alternatively, said products may be isomerized and hydrogenated to form saturated linear alcohols of the formula:

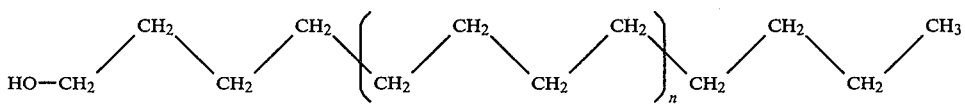

where n has the same meaning. This can be done by isomerizing the product of formula ("A") in dioxane as a solvent at a temperature of about 100° C. over a catalyst of palladium, acetylacetonate and triphenylphosphine and then hydrogenated as above to produce saturated linear alcohols of the above formula.

These saturated linear alcohols are precursors of biodegradable detergents, which can be prepared by reaction of the alcohol with ethylene oxide at a temperature of about 140° C. to provide a non-ionic detergent. Those saturated alchohols having a formula RCH₂OH can also be converted to ionic detergents by reaction with sulfuric chlorohydride (HCl-SO₃) to produce compounds of the formula RCH₂—O—SO₃H which can be neutralized with a base, such as ammonia, to produce an ionic detergent of the formula $RCH_2-O-SO_3NH_4$.

The compounds of formula "A" can also be isomerized to form ketones of the following formula:

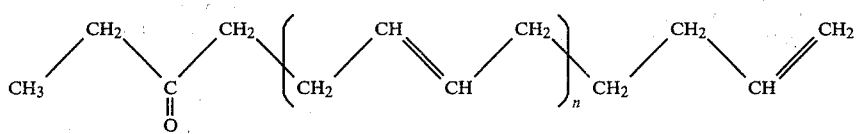

or isomerized and hydrogenated to form ketones of the following formula:

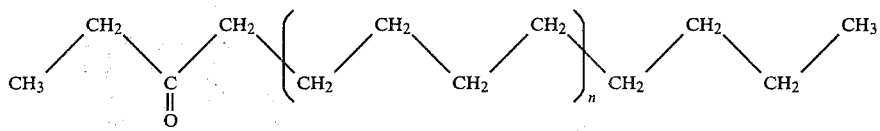

In both of these formulae, $n=2$ or $4$. This can be done by isomerizing the compound of formula "A" at a temperature of about 110° C. over a catalyst of palladium or platinum on a carbon black support or a catalyst of hydridochlorotris (triphenylphosphine) ruthenium. Similarly, the products of formula "A" can be subjected to this same isomerization as just described and then hydrogenated as described above for the production of saturated linear alcohols.

The process of the invention is preferably, but not necessarily, carried out in an oxygen-free atmosphere.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLES 1 TO 8

80 mg. of palladium acetate (0.35 mg. atom of Pd) and 1 g. (16 millimols) of boric acid were introduced into a thick-walled glass tube and agitated by a Teflon-coated bar, driven by a magnetic agitator. The tube was purged three times by a vacuum-argon system and thereupon 10 g. of dimethylformamide, the amount of water indicated in Table I, below, and 4.5 g. of butadiene (92 millimols) were added one after the other.

Agitation of the contents was effected for 24 hours at 20° C. Analysis by gaseous-phase chromatography showed that the following four products (I to IV) were obtained:

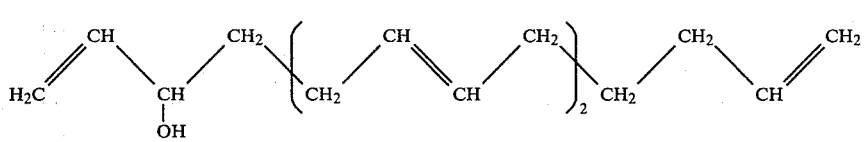

(Hexadeca-1,6,10,15-tetraene-3-ol)

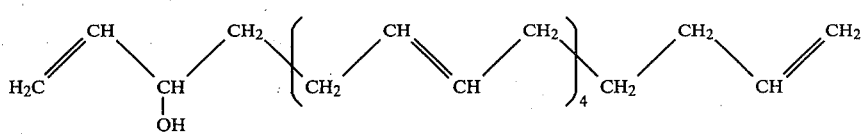

(Tetra-1,6,10,14,18,23-hexane-3-ol)

(III) oligomerization products of butadiene; and (IV) polymerization products of butadiene having more than 24 carbon atoms.

These compounds can be separated from each other by any technique well-known to the man skilled in the art, such as, for instance, distillation under reduced pressure.

The results obtained are given in Table I, below.

In a number of the examples which follow and in a number of the tables which follow, the products obtained will be referred to by Nos. I, II, III and IV, which will be employed to indicate the products as identified by the same numbers above.

EXAMPLES 9 TO 14

The same procedure of Example 1 was repeated, but varying amounts of boric acid and water as indicated in Table II, below, were employed. The results obtained are indicated in Table II, below.

EXAMPLES 15 TO 18

The procedure of Example 1 was repeated, but increasing the amount of solvent (dimethylformamide) from 10 to 15 g. and using either 1 g. or 2 g. of boric acid with variable amounts of water as indicated in Table III, below. The results obtained are given in said Table III, below.

EXAMPLES 19 TO 22

The procedure of Example 1 was repeated, but with a molar ratio of H₂O to B(OH)₃ of 4 and using the different catalysts indicated in Table IV, below, which table also sets forth the results obtained.

EXAMPLE 23

The procedure of Example 1 was repeated, but employing a molar ratio of H₂O to B(OH)₃ of 4 and adding 29.6 mg. of triphenylphosphine of the formula:

(0.113 milligram atom of P³⁺).

The conversion rate of the butadiene was 27.4%. There were obtained:

| Compound No. | Amount |
| --- | --- |
| I | 0.560 g. |
| II | 0.095 g. |
| III | 0.142 g. |
| IV | 0.323 g. |

EXAMPLE 24

The procedure of Example 23 was repeated, but adding, instead of triphenylphosphine, 57.8 g. of metasulfonated triphenylphosphine of the formula:

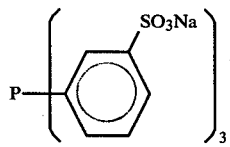

(0.094 milligram atom of P³⁺).

The conversion rate of the butadiene was 34.2% There was obtained:

| Compound No. | Amount |
| --- | --- |
| I | 0.629 g. |
| II | 0.149 g. |
| III | 0.161 g. |
| IV | 0.400 g. |

EXAMPLES 25-27

The procedure of Example 1 was repeated, but with a ratio of H₂O to B(OH)₃ of 4, but varying the nature of the solvent (in each case 10 g. of solvent was used). The solvents employed and results obtained are set forth in Table V, below.

EXAMPLES 28 TO 34

The procedure of Example 1 was repeated, but with a molar ratio of H₂O to B(OH)₃ of 4, and also varying the amount of palladium acetate. The results are set forth in Table VI, below.

EXAMPLES 35 TO 37

The procedure of Example 1 was repeated, but with a molar ratio of H₂O to B(OH)₃ of 4, and also varying the temperatures. The results are set forth in Table VII, below.

EXAMPLES 38 TO 40

The procedure of Example 1 was repeated, but with a molar ratio of H₂O to B(OH)₃ of 4, and also varying the butadiene concentrations. The results are set forth in Table VIII, below.

EXAMPLES 41 TO 50

The procedure of Example 1 was repeated, but using a molar ratio of H₂O to B(OH)₃ of 2 (Table IX, below, for Examples 41 to 45) or else 4 (Table X, below, for Examples 46 to 50) and varying the reaction times. The results are shown in Tables IX and X, below.

EXAMPLE 51

1.20 g. (5.34 milligram atoms of Pd) of palladium acetate and 15 g. (242 millimols) of orthoboric acid were introduced into an 0.5 liter stainless steel autoclave. It was purged three times by a vacuum-argon system and 164 g. of dimethylformamide, 17.64 g. of water (0.98 mol) and 62 g. of butadiene (1.15 mol) were then added one after the other. Agitation was effected at 20° C. for 24 hours. The conversion rate of the butadiene was 41%. After addition of water and neutralization of the boric acid by sodium bicarbonate, 27 g. of organic phase were obtained, analysis of which by gaseous-phase chromatography shows that it contains:

| Compound No. | Amount |
| --- | --- |
| I | 10.08 g. |
| II | 3 g. |
| III | 1.31 g. |
| IV | 11.29 g. |

EXAMPLES 52 TO 58

80 mg. of palladium acetate (0.35 milligram atom of Pd), 1 g. (16 millimols) of othoboric acid and an amount of carboxylic acid, such that the atomic ratio H+/Pd was equal to 2, were added to a thick-walled glass tube which was stirred by a Teflon-coated bar driven by a magnetic agitator. The tube was purged three times by a vacuum-argon system and thereupon there were introduced, in succession, 10 g. of dimethylformamide, 1.2 g. of water (molar ratio H₂O/B(OH)₃=4) and 4.5 g. of butadiene (92 millimols).

Agitation was effected for 24 hours at 25° C.

The results obtained are indicated in Tables XI and XIA, below.

EXAMPLE 59

The procedure of Example 1 was repeated, but employing:
Pd (φCOO)₂=0.136 g. (0.36 milligram atom of Pd)
B(OH)₃=1 g.
dimethylformamide=9.3 g.
H₂O=1.18 g.
butadiene=4.6 g.
Heating was effected at 50° C. for 2 hours.

The conversion rate of the butadiene was 37.7%.
There were obtained:

| Compound No. | Amount |
|---|---|
| I | 0.807 g. |
| II | 0.267 g. |
| III | 0.139 g. |
| IV | 0.501 g. |

EXAMPLE 60

The procedure of Example 59 was repeated, but with heating at 50° C. for 16 hours.

The conversion rate of the butadiene was 63.5%. There were obtained:

| Compound No. | Amount |
|---|---|
| I | 1.140 g. |
| II | 0.333 g. |
| III | 0.239 g. |
| IV | 0.866 g. |

EXAMPLE 61

The procedure of Example 60 was repeated, but using 1.79 g. of $H_2O$.

The conversion rate of the butadiene was 54.8%. There were obtained:

| Compound No. | Amount |
|---|---|
| I | 1.325 g. |
| II | 0.296 g. |
| III | 0.240 g. |
| IV | 0.305 g. |

EXAMPLE 62

The procedure of Example 1 was repeated, but employing:
Pd(AcO)$_2$=81.6 mg. (0.36 milligram atom of Pd)
benzoic acid=88 mg. (0.72 millimol)
$B(OH)_3$=1 g.
dimethylformamide=9.6 g.
$H_2O$=1.23 g.
butadiene=4.7 g.

Heating was effected at 50° C. for 2 hours.
The conversion rate of the butadiene was 34%.
There were obtained:

| Compound No. | Amount |
|---|---|
| I | 0.815 g. |
| II | 0.206 g. |
| III | 0.186 g. |
| IV | 0.335 g. |

EXAMPLE 63

The procedure of Example 62 was repeated, but using 1.78 g. of $H_2O$.

The conversion rate of the butadiene was 21.3%.
There were obtained:

| Compound No. | Amount |
|---|---|
| I | 0.506 g. |
| II | 0.111 g. |
| III | 0.162 g. |
| IV | 0.149 g. |

EXAMPLE 64

Into a 125 ml. stainless steel autoclave there were introduced:
Pd(AcO)$_2$=0.238 g. (1.06 milligram atom of Pd)
benzoic acid=0.263 g. (2.15 millimols)
$B(OH)_3$=3 g.
dimethylformamide=28.5 g.
$H_2O$=3.6 g.
butadiene=16 g.

Heating was effected with agitation at 65° C. for 1 hour.
The conversion rate of the butadiene was 30.4%.
There were obtained:

| Compound No. | Amount |
|---|---|
| I | 2.292 g. |
| II | 0.693 g. |
| III | 0.714 g. |
| IV | 0.918 g. |

EXAMPLE 65

The procedure of Example 1 was repeated, but using:
Pd(AcO)$_2$=0.080 g. (0.35 milligram atom of Pd)
benzoic acid=0.187 g. (1.53 millimols)
$B(OH)_3$=1 g.
dimethylformamide=9.7 g.
$H_2O$=1.20 g.
butadiene=4.6 g.

Heating was effected at 50° C. for 4 hours.
The conversion rate of the butadiene was 25.8%
There were obtained:

| Compound No. | Amount |
|---|---|
| I | 0.702 g. |
| II | 0.118 g. |
| III | 0.159 g. |
| IV | 0.156 g. |

EXAMPLE 66

The procedure of Example 65 was repeated, but heating at 50° C. for 16 hours.

The conversion rate of the butadiene was 55.6%.
There were obtained:

| Compound No. | Amount |
|---|---|
| I | 1.333 g. |
| II | 0.167 g. |
| III | 0.286 g. |
| IV | 0.393 g. |

EXAMPLE 67

The procedure of Example 66 was repeated, but using 1.8 g. of $H_2O$.

The conversion rate of the butadiene was 35%.
There were obtained:

| Compound No. | Amount |
|---|---|
| I | 0.921 g. |
| II | 0.08 g. |
| III | 0.161 g. |
| IV | 0.0 g. |

EXAMPLE 68

The procedure of Example 67 was repeated, but heating at 65° C. for 2 hours.
The conversion rate of the butadiene was 29.1%.
There were obtained:

| Compound No. | Amount |
|---|---|
| I | 0.757 g. |
| II | 0.110 g. |
| III | 0.193 g. |
| IV | 0.035 g. |

EXAMPLE 69

The procedure of Example 64 was repeated, but using:
Pd(AcO)$_2$ = 0.162 g. (0.724 milligram atom of Pd)
benzoic acid = 0.361 g. (2.96 millimols)
B(OH)$_3$ = 2 g.
dimethylformamide = 19 g.
H$_2$O = 3.6 g.
butadiene = 10 g.
Heating was effected at 80° C. for 1 hour.
The conversion rate of the butadiene was 31.4%.
There were obtained:

| Compound No. | Amount |
|---|---|
| I | 1.59 g. |
| II | 0.254 g. |
| III | 0.572 g. |
| IV | 0.230 g. |

EXAMPLE 70

The procedure of Example 69 was repeated, but using 0.110 g. of palladium acetate (0.49 milligram atom of Pd) and 0.243 g. of benzoic acid (2 millimols).
The conversion rate of the butadiene was 27.1%.
There were obtained:

| Compound No. | Amount |
|---|---|
| I | 1.196 g. |
| II | 0.190 g. |
| III | 0.335 g. |
| IV | 0.097 g. |

EXAMPLE 71

The procedure of Example 64 was repeated, but using:
Pd(AcO)$_2$ = 0.166 g. (0.74 milligram atom of Pd)
benzoic acid = 0.361 g. (2.96 millimols)
B(OH)$_3$ = 4 g.
dimethylformamide = 28.5 g.
H$_2$O = 7 g.
butadiene = 11 g.
Heating was effected with agitation at 95° C. for 30 minutes.
The conversion rate of the butadiene was 44.1%.
There were obtained:

| Compound No. | Amount |
|---|---|
| I | 1.807 g. |
| II | 0.413 g. |
| III | 1.179 g. |
| IV | 0.413 g. |

EXAMPLE 72

The procedure of Example 71 was repeated, but using 0.152 g. of palladium acetate (0.68 milligram atom of Pd), 0.334 g. of benzoic acid (2.73 millimols) and 14 g. of butadiene.
Heating was effected at 80° C. for 1 hour.
The conversion rate of the butadiene was 29.1%.
There were obtained:

| Compound No. | Amount |
|---|---|
| I | 2.06 g. |
| II | 0.242 g. |
| III | 0.643 g. |
| IV | 0.428 g. |

TABLE I

| Examples | Amount of water (g) | Molar ratio H$_2$O/B(OH)$_3$ | Conversion rate of butadiene (%) | Products obtained (g) | | | |
|---|---|---|---|---|---|---|---|
| | | | | I | II | III | IV |
| 1 | 0 | 0 | 3.5 | 0 | 0 | 0.1 | 0 |
| 2 | 0.14 | 0.48 | 11.5 | 0.230 | 0.058 | 0.079 | 0.112 |
| 3 | 0.29 | 1 | 30.3 | 0.481 | 0.2 | 0.095 | 0.605 |
| 4 | 0.62 | 2.1 | 34.9 | 0.413 | 0.22 | 0.113 | 0.875 |
| 5 | 1.09 | 3.65 | 34 | 0.572 | 0.22 | 0.084 | 0.668 |
| 6 | 1.2 | 4.2 | 31.9 | 0.514 | 0.157 | 0.081 | 0.64 |
| 7 | 1.85 | 6.5 | 28.7 | 0.573 | 0.133 | 0.130 | 0.49 |
| 8 | 2.8 | 9.45 | 21 | 0.397 | 0.13 | 0.119 | 0.24 |

TABLE II

| Examples | Amount of B(OH)$_3$ (g) | Amount of water (g) | Molar ratio H$_2$O/B(OH)$_3$ | Conversion rate of butadiene (%) | Products obtained (g) | | | |
|---|---|---|---|---|---|---|---|---|
| | | | | | I | II | III | IV |
| 9 | 0 | 0 | 0 | 0 | 0 | 0 | 0 | 0 |
| 10 | 0.5 | 0.3 | 2.04 | 32 | 0.192 | 0.150 | 0.10 | 1 |
| 11 | 1.01 | 0.55 | 1.86 | 46.7 | 0.832 | 0.268 | 0.10 | 1.05 |

TABLE II-continued

| Examples | Amount of B(OH)$_3$ (g) | Amount of water (g) | Molar ratio H$_2$O/B(OH)$_3$ | Conversion rate of butadiene (%) | Products obtained (g) I | II | III | IV |
|---|---|---|---|---|---|---|---|---|
| 12 | 2.01 | 1.34 | 2.28 | 23 | 0.695 | 0.160 | 0.02 | 0.30 |
| 13 | 2.09 | 2.36 | 3.9 | 15.4 | 0.36 | 0.091 | 0.12 | 0.246 |
| 14 | 1.96 | 3.43 | 6 | 15.9 | 0.358 | 0.018 | 0.08 | 0.17 |

TABLE III

| Examples | Amount of B(OH)$_3$ (g) | Amount of H$_2$O (g) | Molar ratio H$_2$O/B(OH)$_3$ | Conversion rate of butadiene (%) | Products obtained (g) I | II | III | IV |
|---|---|---|---|---|---|---|---|---|
| 15 | 1 | 1.1 | 3.7 | 25 | 0.197 | 0.06 | 0.026 | 0.757 |
| 16 | 1 | 1.67 | 5.5 | 35.7 | 0.612 | 0.164 | 0.056 | 0.680 |
| 17 | 2 | 2.49 | 4.2 | 21.8 | 0.533 | 0.136 | 0.029 | 0.330 |
| 18 | 2 | 3.73 | 6.7 | 22.7 | 0.663 | 0.090 | 0.088 | 0.266 |

TABLE IV

| Example | Catalyst Nature | Amount (g) | Number of milli-gram atoms of Pd | Conversion rate of butadiene % | Products obtained (g) I | II | III | IV |
|---|---|---|---|---|---|---|---|---|
| 19 | Pd(CH$_3$—COO)$_2$ | 0.08 | 0.35 | 47.0 | 0.897 | 0.271 | 0.090 | 0.944 |
| 20 | 1 | 0.107 | 0.4 | 55 | 0.392 | 0.264 | 0.037 | 1.48 |
| 21 | 2 | 0.063 | 0.306 | 27.8 | 0.486 | 0.130 | 0.024 | 1.10 |
| 22 | ($\phi$-COO)$_2$Pd | 0.121 | 0.325 | 37.2 | 0.943 | 0.221 | 0.094 | 0.419 |

1 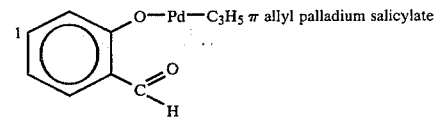 $\pi$ allyl palladium salicylate 2 (CH$_3$—COO Pd C$_3$H$_5$)$_2$ bis-($\pi$-allyl palladium acetate)

TABLE V

| Example | Nature of solvent | Conversion rate of butadiene % | Products obtained (g) I | II | III | IV |
|---|---|---|---|---|---|---|
| 25 | Dimethylformamide | 47 | 0.897 | 0.271 | 0.090 | 0.944 |
| 26 | N—methylpyrrolidone | 27.4 | 0.522 | 0.101 | 0.104 | 0.408 |
| 27 | propyl carbonate | 5 | 0.028 | 0.045 | 0.010 | 0.355 |

TABLE VI

| Example | Concentration of Pd (ppm) | Amount of Pd acetate (mg) | Number of milligram-atoms of Pd | Conversion rate of butadiene (%) | Products obtained (g) I | II | III | IV |
|---|---|---|---|---|---|---|---|---|
| 28 | 760 | 26.5 | 0.118 | 10.7 | 0.230 | 0.045 | 0.018 | 0.175 |
| 29 | 1320 | 46.5 | 0.207 | 23.4 | 0.456 | 0.116 | 0.046 | 0.39 |
| 30 | 2250 | 79.5 | 0.35 | 47 | 0.897 | 0.271 | 0.090 | 0.944 |
| 31 | 3000 | 105.6 | 0.470 | 58.3 | 1.034 | 0.343 | 0.139 | 1.164 |
| 32 | 4000 | 140.8 | 0.627 | 68.3 | 1.198 | 0.414 | 0.192 | 1.315 |
| 33 | 4500 | 158 | 0.705 | 74.4 | 1.159 | 0.468 | 0.212 | 1.414 |
| 34 | 5070 | 180 | 0.800 | 77.2 | 1.216 | 0.468 | 0.253 | 1.653 |

TABLE VII

| Example | Temperature (°C.) | Conversion rate of butadiene (%) | Products obtained (g) I | II | III | IV |
|---|---|---|---|---|---|---|
| 35 | 10 | 11 | 0.139 | 0.036 | 0.020 | 0.315 |
| 36 | 35 | 63.2 | 1.089 | 0.354 | 0.231 | 1.263 |
| 37 | 50 | 66.6 | 0.771 | 0.419 | 0.323 | 1.491 |

TABLE VIII

| Example | Amount of butadiene (g) | Conversion rate (%) | Products obtained (g) I | II | III | IV |
|---|---|---|---|---|---|---|
| 38 | 2.48 | 36.8 | 0.592 | 0.151 | 0.080 | 0.450 |
| 39 | 4.5 | 31.9 | 0.514 | 0.157 | 0.081 | 0.638 |
| 40 | 9.65 | 12.6 | 0.500 | 0.150 | 0.077 | 0.520 |

TABLE IX

| Examples | Reaction time (hours) | Conversion rate of butadiene (%) | Products obtained (g) I | II | III | IV |
|---|---|---|---|---|---|---|
| 41 | 5 | 13.2 | 0.235 | 0.090 | 0.043 | 0.38 |
| 42 | 7 | 25.9 | 0.351 | 0.154 | 0.055 | 0.48 |
| 43 | 17 | 39 | 0.972 | 0.220 | 0.083 | 0.56 |
| 44 | 41 | 51 | 0.665 | 0.254 | 0.110 | 0.823 |
| 45 | 95 | 54.7 | 0.405 | 0.364 | 0.130 | 1.56 |

TABLE X

| Examples | Reaction time (hours) | Conversion rate of butadiene (%) | Products obtained (g) | | | |
|---|---|---|---|---|---|---|
| | | | I | II | III | IV |
| 46 | 7 | 12.6 | 0.23 | 0.075 | 0.030 | 0.260 |
| 47 | 16 | 26.5 | 0.47 | 0.140 | 0.050 | 0.520 |
| 48 | 24 | 31.9 | 0.51 | 0.157 | 0.081 | 0.638 |
| 49 | 40 | 43 | 0.833 | 0.310 | 0.170 | 0.960 |
| 50 | 96 | 48.7 | 0.861 | 0.340 | 0.200 | 1.050 |

TABLE XI

| Examples | Acid Added type | weight (mg) | Conversion rate of butadiene (%) | Products obtained (g) | | | |
|---|---|---|---|---|---|---|---|
| | | | | I | II | III | IV |
| 52 | phenyl-COOH | 87.2 | 27.4 | 0.679 | 0.124 | 0.074 | 0.31 |
| 53 | 2-methylphenyl-COOH | 98 | 30 | 0.684 | 0.150 | 0.103 | 0.228 |
| 54 | 4-methylphenyl-COOH | 95 | 25.2 | 0.636 | 0.098 | 0.052 | 0.333 |
| 55 | 4-hydroxyphenyl-COOH | 94 | 31.1 | 0.770 | 0.159 | 0.074 | 0.453 |

TABLE XIA

| Examples | Acid added type | weight (mg) | Conversion rate of butadiene (%) | Products obtained (g) | | | |
|---|---|---|---|---|---|---|---|
| | | | | I | II | III | IV |
| 56 | naphthyl-COOH | 130 | 11 | 0.266 | 0.029 | 0.075 | 0.069 |
| 57 | cyclohexyl-COOH | 93 | 32.3 | 0.705 | 0.200 | 0.151 | 0.491 |
| 58 | (CH$_3$)$_3$C-COOH | 82 | 29.5 | 0.535 | 0.103 | 0.081 | 0.595 |

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. An unsaturated fatty alcohol of the formula:

$$H_2C\!=\!\!\!\overset{CH}{\underset{CH(OH)}{}}\!\!-CH_2-\!\left[CH_2-\overset{CH}{\underset{CH_2}{}}\!\!=\!\!\overset{CH}{\underset{}{}}\!-CH_2\right]_n\!\!-CH_2-CH\!=\!CH_2$$

in which n=2 or 4.

2. Hexadeca-1,6,10,15-tetraene-3-ol.
3. Tetracosa-1,6,10,14,18,23-hexaene-3-ol.

* * * * *

UNITED STATES PATENT AND TRADEMARK OFFICE
CERTIFICATE OF CORRECTION

PATENT NO. : 4,424,399
DATED : January 3, 1984
INVENTOR(S) : Didier Morel

It is certified that error appears in the above-identified patent and that said Letters Patent is hereby corrected as shown below: Column 3, lines 6-25,

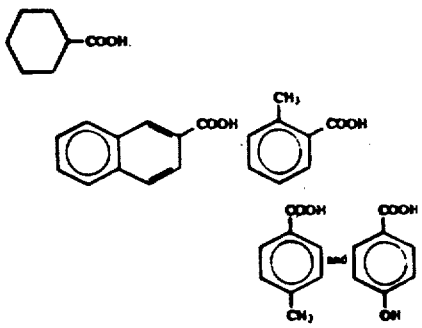

should be

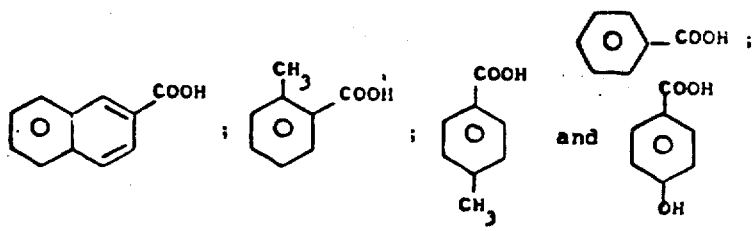

Signed and Sealed this

Seventeenth Day of December 1985

[SEAL]

Attest:

DONALD J. QUIGG

Attesting Officer    Commissioner of Patents and Trademarks